United States Patent
Roeder (10) Patent No.: US 9,808,364 B2
(45) Date of Patent: Nov. 7, 2017

(54) SYSTEMS AND METHODS FOR MAINTAINING PERFUSION OF BRANCH VESSELS

(71) Applicant: COOK MEDICAL TECHNOLOGIES LLC, Bloomington, IN (US)

(72) Inventor: Blayne A. Roeder, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 194 days.

(21) Appl. No.: 13/793,695

(22) Filed: Mar. 11, 2013

(65) Prior Publication Data

US 2014/0257453 A1 Sep. 11, 2014

(51) Int. Cl.
| | |
|---|---|
| A61F 2/954 | (2013.01) |
| A61F 2/82 | (2013.01) |
| A61F 2/856 | (2013.01) |
| A61F 2/07 | (2013.01) |
| A61F 2/24 | (2006.01) |
| A61F 2/844 | (2013.01) |
| A61F 2/06 | (2013.01) |
| A61F 2/95 | (2013.01) |

(52) U.S. Cl.
CPC ............ *A61F 2/954* (2013.01); *A61F 2/07* (2013.01); *A61F 2/82* (2013.01); *A61F 2/856* (2013.01); *A61F 2/2418* (2013.01); *A61F 2/844* (2013.01); *A61F 2002/061* (2013.01); *A61F 2002/067* (2013.01); *A61F 2002/9511* (2013.01)

(58) Field of Classification Search
CPC .............. A61F 2002/067; A61F 2/2418; A61F 2230/0054; A61F 2002/9511; A61F 2/89; A61F 2/95; A61F 2/92; A61F 2002/9505; A61F 2/954; A61F 2/07; A61F 2002/072; A61F 2002/075; A61F 2002/077; A61F 2/856; A61F 2/86; A61F 2002/91591; A61F 2/82; A61F 2/08
USPC .................................... 623/1.11, 1.12, 1.13
See application file for complete search history.

(56) References Cited

U.S. PATENT DOCUMENTS 5,387,235 A * 2/1995 Chuter ..................... 623/1.11
5,720,776 A * 2/1998 Chuter et al. .............. 623/1.36
(Continued)

FOREIGN PATENT DOCUMENTS

WO WO2010/113138 10/2010

OTHER PUBLICATIONS

Extended European Search Report for EP 14 27 5047 dated Jul. 10, 2014, 5 pgs.
(Continued)

*Primary Examiner* — Tuan V Nguyen
*Assistant Examiner* — Chima Igboko
(74) *Attorney, Agent, or Firm* — Brinks Gilson & Lione (57) ABSTRACT

An endoluminal prosthesis comprises a graft having a tubular body comprising proximal and distal ends, inner and outer surfaces, and partially and fully deployed states. A temporary channel is disposed external to the outer surface of the graft in the partially deployed state. The temporary channel begins at one of the proximal and distal ends of the graft, and extends along only a portion of a longitudinal length of the graft. The temporary channel is removed when the graft is in a fully deployed state.

18 Claims, 5 Drawing Sheets

(56) References Cited

U.S. PATENT DOCUMENTS

| | | | |
|---|---|---|---|
| 5,843,162 A * | 12/1998 | Inoue | 623/1.13 |
| 5,873,906 A * | 2/1999 | Lau et al. | 128/898 |
| 5,948,017 A * | 9/1999 | Taheri | 623/1.14 |
| 6,613,072 B2 * | 9/2003 | Lau et al. | 623/1.11 |
| 7,018,408 B2 * | 3/2006 | Bailey et al. | 623/2.11 |
| 7,722,657 B2 * | 5/2010 | Hartley | 623/1.13 |
| 8,167,930 B2 * | 5/2012 | Allen et al. | 623/1.35 |
| 8,753,385 B2 * | 6/2014 | Hartley et al. | 623/1.11 |
| 8,758,425 B2 * | 6/2014 | Greenberg et al. | 623/1.12 |
| 8,771,333 B2 * | 7/2014 | Rincon | 623/1.11 |
| 8,808,356 B2 * | 8/2014 | Braido et al. | 623/1.26 |
| 2002/0040236 A1 * | 4/2002 | Lau et al. | 623/1.12 |
| 2003/0204243 A1 * | 10/2003 | Shiu | 623/1.16 |
| 2004/0073289 A1 * | 4/2004 | Hartley | 623/1.13 |
| 2006/0004433 A1 * | 1/2006 | Greenberg | A61F 2/07 623/1.11 |
| 2007/0168013 A1 * | 7/2007 | Douglas | A61F 2/07 623/1.12 |
| 2009/0270971 A1 * | 10/2009 | Xiao et al. | 623/1.14 |
| 2010/0114291 A1 * | 5/2010 | Kolbel et al. | 623/1.12 |
| 2010/0268318 A1 * | 10/2010 | Glynn | A61F 2/07 623/1.13 |
| 2011/0270376 A1 * | 11/2011 | Hartley | 623/1.11 |
| 2012/0150274 A1 * | 6/2012 | Shalev et al. | 623/1.12 |
| 2013/0079870 A1 * | 3/2013 | Roeder et al. | 623/1.35 |

OTHER PUBLICATIONS

EP Examination Report in related application No. 14 275 047.0-1662 dated Jun. 13, 2016 (4 pgs).

* cited by examiner

SYSTEMS AND METHODS FOR MAINTAINING PERFUSION OF BRANCH VESSELS

BACKGROUND

The present embodiments relate to implantable medical devices and methods, and more particularly to systems and methods for maintaining perfusions of branch vessels.

The aortic valve functions as a one-way valve between the heart and the rest of the to body. Blood is pumped from the left ventricle of the heart, through the aortic valve, and into the aorta, which in turn supplies blood to the body. Between heart contractions the aortic valve closes, preventing blood from flowing backwards into the heart.

Damage to the aortic valve can occur from a congenital defect, the natural aging process, and from infection or scarring. Over time, calcium may build up around the aortic valve causing the valve not to open and close properly. Certain types of damage may cause the valve to "leak," resulting in "aortic insufficiency" or "aortic regurgitation." Aortic regurgitation causes extra workload for the heart, and can ultimately result in weakening of the heart muscle and eventual heart failure.

After the aortic valve becomes sufficiently damaged, the valve may need to be replaced to prevent heart failure and death. One approach involves an invasive open procedure. However, patients undergoing such procedure are subjected to a heart-lung bypass, induced cardiac arrest, and extensive trauma to the valve and ascending aorta, and therefore morbidity and mortality rates are relatively high.

A more recent approach involves endovascularly introducing an aortic valve replacement. However, current endovascular approaches do not allow for sufficient repair of both the aortic valve and the ascending aorta, due to the complex anatomy in this region including the valvular sinus and the coronary arteries. Moreover, attempts to endovascularly repair the aortic valve and the ascending aorta may encompass risks of temporary blocking flow to the coronary arteries during the procedure, which can cause significant complications for a patient.

SUMMARY

An endoluminal prosthesis comprises a graft having a tubular body comprising proximal and distal ends, inner and outer surfaces, and partially and fully deployed states. A temporary channel is disposed external to the outer surface of the graft in the partially deployed state. The temporary channel begins at one of the proximal and distal ends of the graft, and extends along only a portion of a longitudinal length of the graft. The temporary channel is removed when the graft is in the fully deployed state.

In one embodiment, the temporary channel may begin at the distal end of the graft and terminate before the proximal end of the graft. At least one fenestration may be disposed in a sidewall of the graft between the proximal and distal ends of the graft, and a proximal end of the temporary channel may be aligned with the fenestration. A valve replacement may be disposed between the proximal and distal ends of the graft. The temporary channel may comprise a "U"-shape.

In one embodiment, a shape of the temporary channel may be maintained by securement of a first portion of the graft to a second portion of the graft, for example, using at least one suture. In other embodiments, a shape of the temporary channel may be maintained by securement of a portion of the graft to a delivery system, for example, by securing a wire extending along the delivery system to a coupling member of the graft.

In other embodiments, the temporary channel comprises a sheath having an aperture. The aperture is disposed distal to the distal end of the graft in the partially deployed state, and a portion of the sheath is disposed adjacent to the outer surface of the graft in the partially deployed state. In a further alternative, the temporary channel may comprise a removable stent framework disposed exterior to the graft.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Referring to FIGS. 1-5, an endoluminal prosthesis 10 is shown and described. The prosthesis 10 comprises a graft 20 having a tubular body comprising proximal and distal ends 22 and 24, and a lumen 18 extending therebetween.

Figure 1:
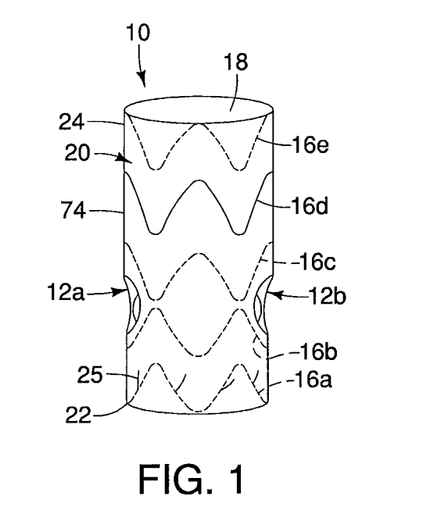
FIG. 1 is a side view of an endoluminal prosthesis comprising a valve replacement.

The prosthesis 10 comprises a valve 60 disposed between the proximal end 22 and the distal end 24 of the graft 20. In one example, the valve 60 can be coupled to the graft 20 with sutures.

In one non-limiting example, the valve 60 may comprise an aortic valve designed to replace the function of the recipient's native damaged or poorly performing aortic valve. In other examples, the prosthesis 10 may be deployed in other arterial locations, i.e., other than the aortic annulus and ascending aorta, or alternatively may be deployed in a patient's venous system, or any suitable duct, passageway or vessel.

Figure 2A:
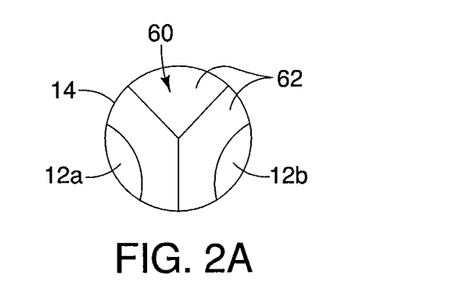
FIGS. 2A-2B are, respectively, top and bottom views of the endoluminal prosthesis of FIG. 1.
Figure 2B:
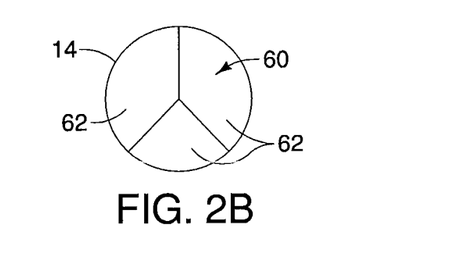

In the non-limiting example of an aortic valve, the valve 60 may be located at the proximal end 22 of the graft 20, closest to the heart. The valve 60 preferably includes one or more leaflets 62, as shown in FIGS. 2A-2B. In this non-limiting example, the valve 60 includes three leaflets 62, though only two leaflets may be used in a "bicuspid" arrangement. The leaflets are arranged in the prosthesis such that the leaflets mimic a naturally occurring aortic valve. The valve 60 "opens" to allow blood flow when the pressure on the proximal side of the valve 60 is greater than pressure on the distal side of the artificial valve. Thus, the valve 60 regulates the unidirectional flow of fluid from the heart into the aorta.

The leaflets of the valve 60 can be fabricated from any at least substantially biocompatible material including such materials as polyester fabrics, polytetrafluoroethylene (PTFE), expanded PTFE, and other synthetic materials known to those of skill in the art. Preferably, the leaflets are fabricated from naturally occurring biomaterials. The leaflets can include a derived collagen material, such as an extracellular matrix. The extracellular matrix can be small intestinal submucosa, stomach submucosa, pericardium, liver basement membrane, urinary bladder submucosa, tissue mucosa, dura mater, or the like.

The prosthesis 10 further comprises at least one stent coupled to the graft 20 that has a contracted delivery state and further has an expanded state for maintaining patency within a portion of the graft. In the exemplary embodiment depicted in FIGS. 1 and 5, five exemplary stents 16a-16e are provided. The stents 16 may be placed on the outer surface and/or inner surface of the graft 20. The exemplary stents 16 of the prosthesis 10 may comprise zig-zag stents or another suitable structure, and may be either self-expanding or balloon expandable.

Figure 5:
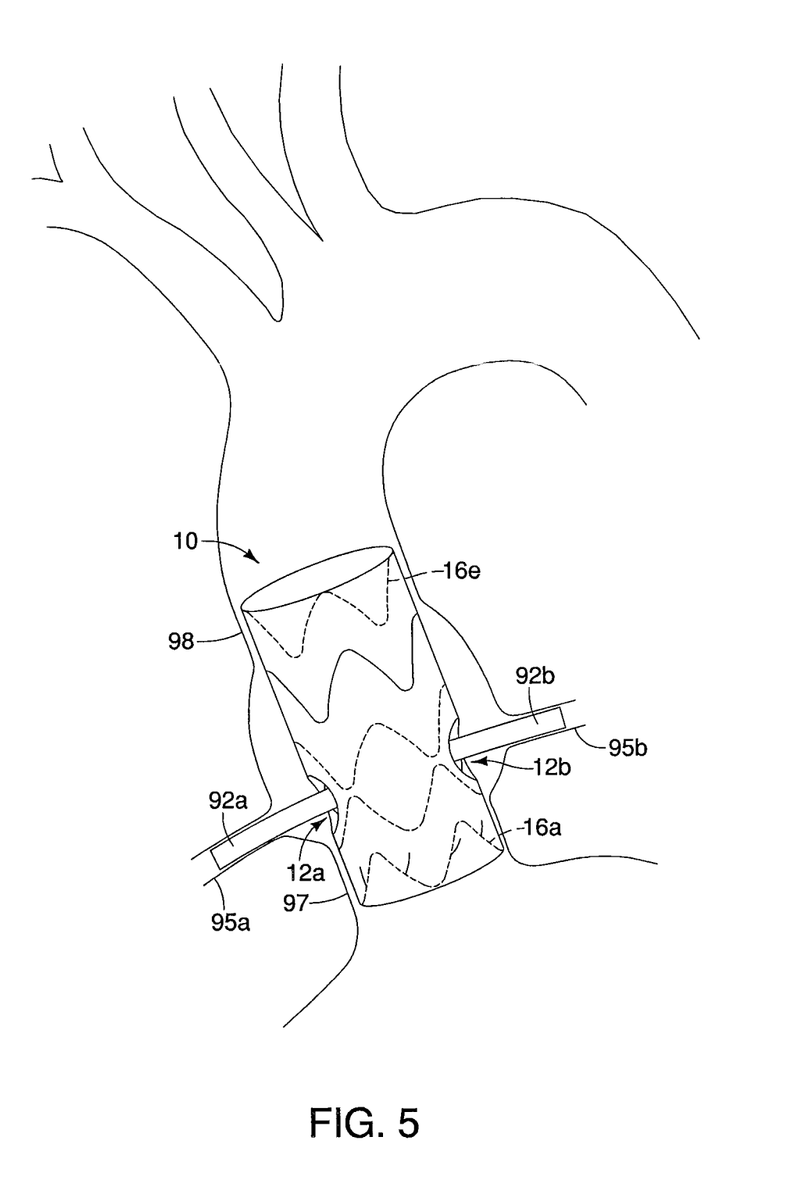
FIG. 5 is a schematic view illustrating deployment of the endoluminal prosthesis of FIG. 1 in a patient's anatomy.

In the embodiment of FIG. 1, a first stent 16a is located at the proximal end of the graft 20. In use, the first stent 16a overlaps with an aortic annulus 97, as shown in FIG. 5. The first stent 16a may comprise a radial force configured to facilitate fixation within the aortic annulus 97 and prevent migration of the proximal end 22 of the graft 20. One or more barbs 25 may be coupled to the first stent 16a to reduce migration of the prosthesis 10.

In the example of FIG. 1, the endoluminal prosthesis 10 comprises second and third z-stents 16b and 16c, which are coupled to the graft 20 such that the distal apices of the second stent 16b are aligned with the proximal apices of the third stent 16c. The fifth stent 16e may be configured to engage a healthy portion of a patient's ascending aorta 98, as depicted in the deployed state of FIG. 5.

The endoluminal prosthesis 10 further comprises at least one fenestration 12 disposed in a sidewall 74 of the graft 20. The one or more fenestrations 12 may be positioned between a proximal apex of the second stent 16b and a distal apex of the third stent 16c. In the embodiment of FIGS. 1-5, first and second fenestrations 12a and 12b are disposed in the sidewall 74 at locations distal to the valve 60, as seen in the top view of FIG. 2A.

The first and second fenestrations 12a and 12b may be provided in accordance with pivoting fenestrations described in detail in U.S. Patent Application Publication Number 2012/0046728, which is hereby incorporated by reference in its entirety. Accordingly, at least one of the fenestrations 12a and 12b is pivotable in any direction away from an axis perpendicular to a longitudinal axis of the prosthesis. In the non-limiting example of FIG. 1, the first and second fenestrations 12a and 12b are disposed in the graft 20 at locations between about 90 and about 270 degrees apart, though the positioning may be greater or less. In the deployed state, a first branch vessel prosthesis 92a may extend between the first fenestration 12a and a first coronary artery 95a in a deployed state, and a second branch vessel prosthesis 92b may extend between the second fenestration 12b and a second coronary artery 95b, when the prosthesis 10 is used to repair an aortic valve, as shown in FIG. 5.

Figure 3:
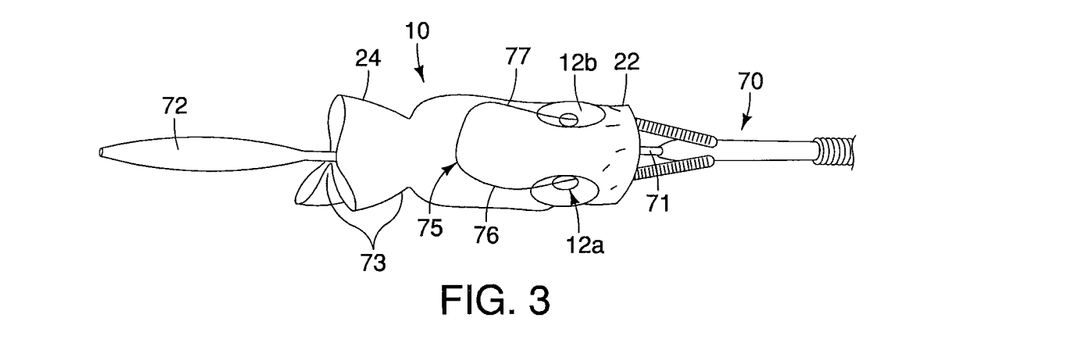
FIGS. 3-4 are side views of an exemplary delivery system that may be used to deliver the endoluminal prosthesis of FIG. 1.

In the examples of FIGS. 1-5, the deployment of the prosthesis 10 into the state shown in FIG. 5 may be achieved in different manners. In one example, the deployment may be made using a transapical or transeptal approach, in which case the prosthesis 10 may be secured to an exemplary delivery system 70 as shown in FIG. 3. In the transapical or transeptal approach, an atraumatic tip 72 of the delivery system is advanced in an antegrade fashion, i.e., in a direction from the aortic annulus 97 towards the ascending aorta 98.

Figure 4:
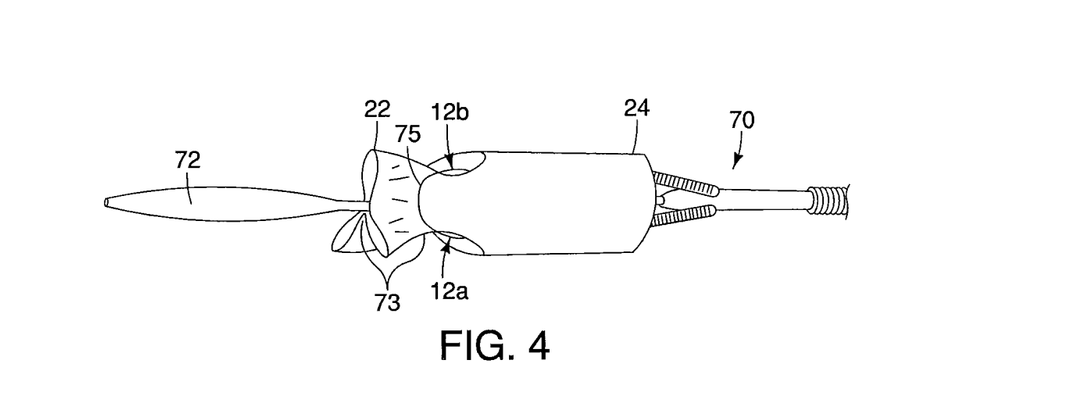

In another example, the deployment may be made using a femoral, carotid, subclavian or axiliary approach, in which case the prosthesis 10 may be secured to the exemplary delivery system 70 as shown in FIG. 4. In this approach, the atraumatic tip 72 of the delivery system 70 is advanced in a retrograde fashion, i.e., in a direction from the ascending aorta 98 towards the aortic annulus 97. In either delivery approach, as shown in FIGS. 3-4, the graft 20 may comprise one or more regions 73 that are radially restrained.

Access to the branch vessels 95a and 95b, such as the coronary arteries, may be provided through the use of a delivery device, such as a catheter. Once a catheter is placed within the branch vessel 95a, a distal portion of the branch vessel prosthesis 92a may be deployed within the branch vessel 95a via balloon expansion or self-expansion into engagement with the branch vessel 95a. Then, a proximal end of the branch vessel prosthesis 92a, remaining within the interior surface of the prosthesis 10, may be flared in order to provide a proper seal between the fenestration 12a and the branch vessel 95a. The second branch vessel prosthesis 92b may be coupled between the prosthesis 10 and the second branch vessel 95b in a similar manner.

Further, the prosthesis 10 may be provided as part of a preloaded system that includes a guide wire 75. In this example, a first end segment 76 of the guide wire 75 may enter the lumen 18 through a proximal or distal end of the prosthesis 10, depending on the delivery orientation of the prosthesis shown in FIG. 3 as compared to FIG. 4. The first end segment 76 exits the graft 20 through the first fenestration 12a. An intermediate segment of the guide wire 75 may extend external of the graft 20 and reenter the lumen 18 of the prosthesis 10 through the second fenestration 12b. A second end segment 77 of the guide wire 75 may extend distally within the lumen 18 and may extend distally to the distal end of the delivery device 70. The first end segment 76 of the guide wire 75 may enable introduction of the first branch prosthesis 92a into the first fenestration 12a to couple the prosthesis 10 to the right coronary artery, and the second end segment 77 of the guide wire 75 may enable introduction of the second branch prosthesis 92b into the second fenestration 12b to couple the prosthesis to the left coronary artery.

Further details of such a preloaded wire, and how it may facilitate deployment of stent-grafts into branch vessels, are described in further detail in U.S. Utility patent application Ser. No. 13/718,915, filed Dec. 18, 2012, which is hereby incorporated by reference in its entirety. While one exemplary delivery system has been shown, it will be appreciated that a number of delivery systems and techniques may be used to deploy the prosthesis 10.

In the deployed state, the first branch vessel prosthesis 92a extends between the first fenestration 12a and the first coronary artery 95a, and the second branch vessel prosthesis 92b extends between the second fenestration 12b and the second coronary artery 95b, as depicted in FIG. 5. Advantageously, if the first and second fenestrations 12a and 12b are not exactly aligned with their respective coronary arteries 95a and 95b for any reason, such as variable patient anatomy, then the pivoting features of the fenestrations 12a and 12b provide the requisite flexibility to allow the branch vessel prostheses 92a and 92b to deploy into the desired position.

The branch vessel prostheses 92a and 92b may be formed from biocompatible materials and may comprise covered stents. Alternatively, they may comprise bare stents. The covered or bare stents may be either self-expanding or balloon expandable. In one embodiment, the branch vessel prostheses 92a and 92b may have both self-expanding and balloon expandable components. If either of the branch vessel prostheses 92a and 92b comprises a covered stent, the graft material used may comprise one or more of the biocompatible materials are discussed above.

Figure 6A:
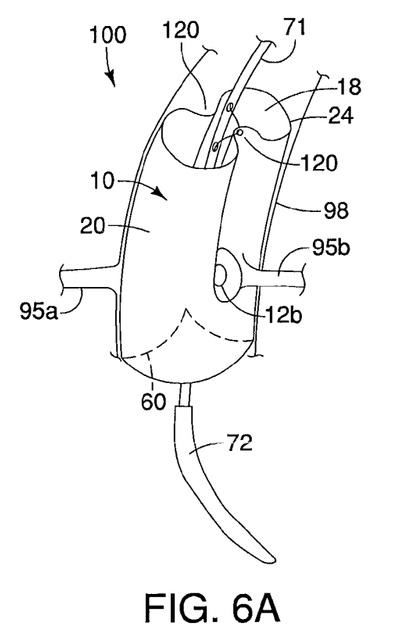
FIGS. 6A-6C are, respectively, a perspective view of an embodiment of a temporary channel when a graft is in a partially deployed state, an enlarged view of a segment of FIG. 6A, and an illustration of the graft in a fully deployed state without the temporary channel.
Figure 6B:
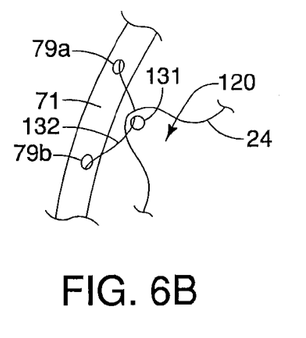
Figure 6C:
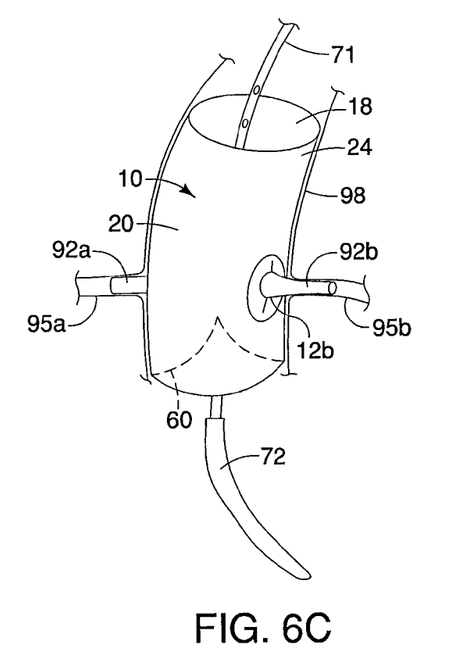

Referring now to FIGS. 6A-6C, a first embodiment of a system 100 for maintaining perfusion of branch vessels is shown and described. The prosthesis 10 and the delivery system 70, described in FIGS. 1-5 above, may be used in conjunction with the system 100 of FIGS. 6A-6C. It should be noted that in the embodiment of FIGS. 6A-6C, as well as the embodiments of FIGS. 7-9 below, the stents 16a-16e coupled to the prosthesis 10—have been omitted for illustrative purposes to show further features associated with FIGS. 6-9.

In the embodiment of FIGS. 6A-6C, the system 100 comprises at least one temporary channel 120, which is formed external to the graft 20. In the example of FIGS. 6A-6C, two temporary channels 120 are shown, one being aligned with the fenestration 12a and the first coronary artery 95a, and the other being aligned with the fenestration 12b and the second coronary artery 95b, as shown in FIG. 6A.

Each temporary channel 120 is disposed external to the outer surface of the graft 20 when the graft 20 is in a partially deployed state, i.e., other than the fully deployed state of FIG. 6C. The temporary channel 120 begins at one of the proximal and distal ends 22 and 24 of the graft 20, and extends along only a portion of a longitudinal length of the graft 20. In the example of FIGS. 6-9, the temporary channel 120 begins at the distal end 24 of the graft 20, and is disposed at a location between the distal end 24 of the graft 20 and one of the fenestration 12. The temporary channel 120 is removed when the graft 20 is in a fully deployed state as shown in FIG. 6C.

The temporary channels 120 may be formed by coupling a portion of the graft 20 to a portion of the delivery system 70. For example, a coupling member 131 in the form of a loop may be secured to the distal end 24 of the graft 20, and a wire 132 may be releasably coupled to the coupling member 131, e.g., disposed through the loop. In one example, the wire 132 may extend along a full length of the delivery system 70, within a catheter 71, and may exit the catheter 71 through a first aperture 79a, then engage the coupling member 131, and then enter back into the catheter 71 through a second aperture 79b that is disposed proximal to the first aperture 79a, as depicted in FIG. 6B. By holding a portion of the graft 20 to the delivery system 70, via the coupling member 131, the temporary channel 120 is formed and may comprise a generally "U"-shaped channel external to the graft 20, as shown in FIG. 6A.

In use, the prosthesis 10 is generally delivered and at least partially deployed into the state shown in FIG. 6A, as described above with respect to FIG. 5. Prior to coupling the branch vessel prostheses 92a and 92b between their respective fenestrations 12a and 12b and coronary arteries 95a and 95b, the temporary channels 120 provide perfusion pathways for fluid flow into the coronary arteries 95a and 95b. In particular, blood may flow in an antegrade manner through the valve 60 and the graft 20, and then flow in a retrograde manner into the temporary channels 120 and into the coronary arteries 95a and 95b. Advantageously, flow may be maintained to the coronary arteries during the endovascular procedure, even though the branch vessel prostheses 92a and 92b have not yet been set in place.

When a physician is ready to introduce or deploy the branch vessel prostheses 92a and 92b to complete the procedure, then the temporary channels 120 may be removed. In the example of FIGS. 6A-6B, the wire 132 may be withdrawn distally beyond the coupling member 131, thereby allowing the associated portion of the graft 20 to self-expand without restraint into full engagement with the ascending aorta 98, as shown in FIG. 6C. Final placement of the branch vessel prostheses 92a and 92b into their respective coronary arteries 95a and 95b then may be completed as described above.

Alternatively, the physician may fully deploy the branch vessel prostheses 92a and 92b into their respective coronary arteries 95a and 95b, even before removing the temporary channels 120. If the system 100 comprises a preloaded delivery system as described above, then it may be easier to deploy the branch vessel prostheses 92a and 92b even when the temporary channel 120 occupies a portion of the ascending aorta 98.

Figure 7A:
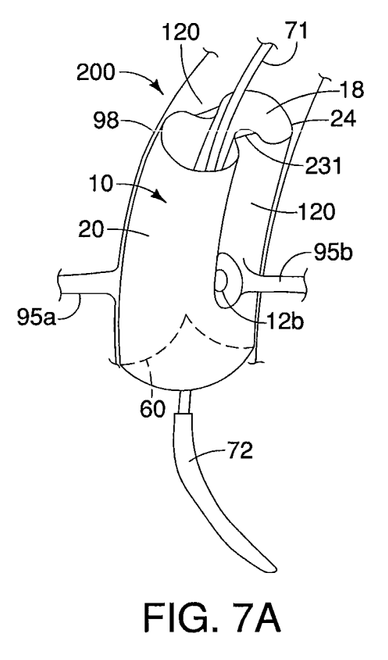
FIGS. 7A-7B are, respectively, a perspective view of an alternative embodiment of a temporary channel, and an enlarged view of a segment of FIG. 7A.
Figure 7B:
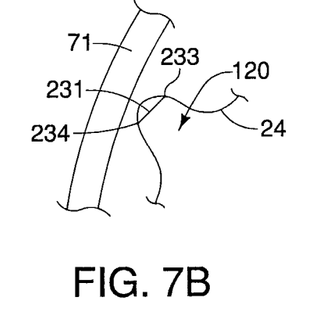

Referring now to FIGS. 7A-7B, an alternative system 200 for maintaining perfusion of branch vessels is shown and described. The system 200 is similar to the system 100 of FIGS. 6A-6B, with a main exception that the graft 20 is secured to itself to form one or more temporary channels 120, as opposed to being secured to the delivery system 70 in the example of FIGS. 6A-6B.

In one non-limiting example, the system 200 comprises at least one suture 231 that is secured to the graft 20 in a manner that forms the shape of the temporary channel 120. For example, the suture 231 may be secured near the distal end 24 of the graft 20 between spaced-apart first and second locations 233 and 234, as depicted in FIG. 7B. The dimensions of the suture 231 and its placement relative to locations 233 and 234 produces a tension that maintains the temporary channel 120 until the suture 231 is released. In one embodiment, multiple sutures 231 may be longitudinally spaced apart between the distal end 24 of the graft 20 and the fenestration 12b, thereby maintaining the temporary channel 120 for a desired longitudinal distance between these locations. The temporary channel 120 may comprise a generally "U"-shaped channel external to the graft 20, as shown in FIGS. 7A-7B.

As an alternative placement, the suture 231 may extend across the lumen 18 of the prosthesis 10, e.g., sewn to distal ends of the graft 20 at two locations spaced apart about 180 degrees. Such a suture across the lumen 18 may hold opposing sides of the graft 20 at a tension that maintains two temporary channels 120 in place, in the manner shown in FIG. 7A, until the suture is released.

As with the prior embodiment of FIGS. 6A-6C, flow may advantageously be maintained to the coronary arteries during the endovascular procedure, even though the branch vessel prostheses 92a and 92b have not yet been set in place. When a physician is ready to introduce or deploy the branch vessel prostheses 92a and 92b to complete the procedure, then the temporary channel 120 may be withdrawn by removal of the suture 231. In one embodiment, the delivery system 70 may comprise a balloon, and radially outward expansion of the balloon against the suture 231 may cause breakage of the suture 231, thereby allowing the associated portion of the graft 20 to self-expand without restraint into full engagement with the ascending aorta 98, as shown in FIG. 6C. Alternatively, the suture 231 may comprise a biodegradable material and may dissolve after a predetermined period of time, thereby allowing the associated portion of the graft 20 to self-expand without restraint into full engagement with the ascending aorta 98. As a further alternative, a trigger wire may be used to remove the suture 231, in a manner similar to that shown in FIGS. 6A-6B above. In any of these techniques, flow is advantageously maintained to the coronary arteries in the interim period required to ensure placement of the branch vessel prostheses 92a and 92b.

Moreover, in the embodiment of FIGS. 7A-7B, in the event that the branch vessel prostheses 92a and 92b cannot be placed into their respective coronary arteries 95a and 95b during an initial procedure, it is possible that the branch vessel prostheses 92a and 92b may be deployed at a later time in a subsequent procedure. In the interim, one or more sutures 231 may maintain the temporary channel 120 to allow sufficient retrograde flow into the coronary arteries 95a and 95b to help sustain the patient while awaiting implantation of the branch prostheses 92a and 92b.

Figure 8:
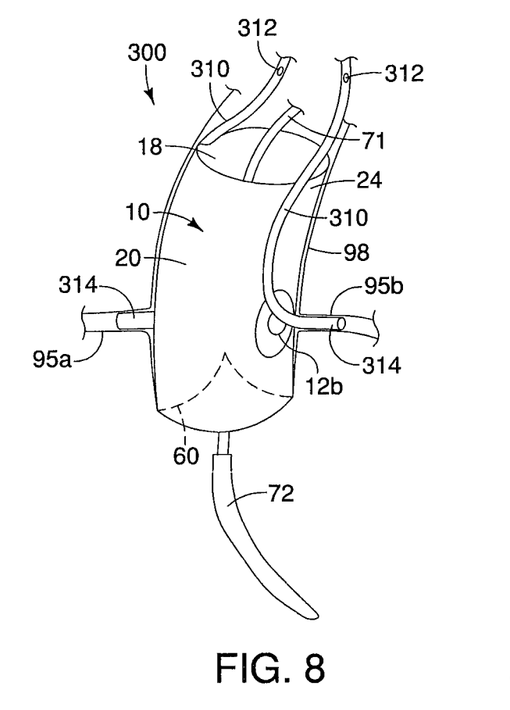
FIG. 8 is a perspective view of a further alternative embodiment of a temporary channel.

Referring now to FIG. 8, an alternative system 300 for maintaining perfusion of branch vessels is shown and described. The system 300 comprises at least one sheath 310 having a proximal end 314, and a distal end (not shown) extending outside of the patient's body. At least one aperture 312 is formed between the proximal and distal ends of the sheath 310. The proximal end 314 of the sheath 310 may be advanced into one of the patient's coronary arteries, as depicted in FIG. 8. The sheath 310 may be delivered via any suitable vessel, including but not limited to the brachiocephalic artery.

The aperture 312 of the sheath 310 is disposed distally beyond the distal end 24 of the graft 20, as the prosthesis 10 is being implanted. At least a portion of the sheath 310 is disposed adjacent to an exterior surface of the graft 20 while the prosthesis 10 is being implanted, and before the branch vessel prostheses 95a and 95b are introduced into their respective coronary arteries. In this manner, blood may flow through the valve 60, through the graft 20, and into the aperture 312, and then flow in a retrograde manner through the sheath 310 and into the coronary artery.

As with the prior embodiments of FIGS. 6-7, flow may advantageously be maintained to the coronary arteries during the endovascular procedure, even though the branch vessel prostheses 92a and 92b have not yet been set in place. When a physician is ready to introduce or deploy the branch vessel prostheses 92a and 92b to complete the procedure, or after the branch vessel prostheses 92a and 92b have been fully implanted, then the sheath 310 may be withdrawn from the patient.

Figure 9:
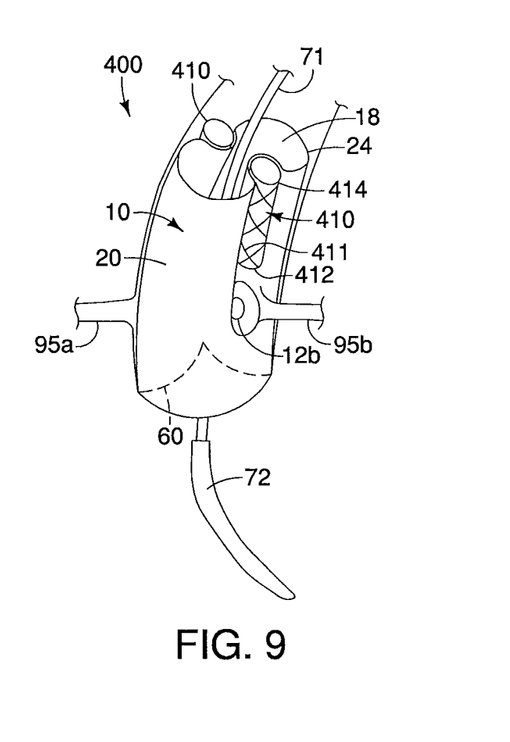
FIG. 9 is a perspective view of yet a further alternative embodiment of a temporary channel.

Referring now to FIG. 9, an alternative system 400 for maintaining perfusion of branch vessels is shown and described. The system 400 comprises at least one external support 410. In this embodiment, the external support 410 is in the form of a stent framework 411 having proximal and distal ends 412 and 414, respectively. The stent framework 411 is disposed adjacent to the outer surface of the graft 20 in a manner such that it forms the shape of the temporary channel 120. For example, the distal end 414 of the stent framework 411 may be disposed near the distal end 24 of the graft 20, and the proximal end 412 of the stent framework 411 may be disposed a short distance distal to the fenestration 12b, as depicted in FIG. 9. The external support 410 may be deployed in conjunction with, or before, the partial deployment of the graft 20 as shown in FIG. 9.

In this manner, at least a portion of the external support 410 is disposed adjacent to an exterior surface of the graft 20 while the prosthesis 10 is being implanted, and before the branch vessel prostheses 95a and 95b are introduced into their respective coronary arteries. Accordingly, blood may flow through the valve 60, through the graft 20, and then flow in a retrograde manner through the support 410 and into the coronary artery.

As with the prior embodiments of FIGS. 6-8, flow may advantageously be maintained to the coronary arteries during the endovascular procedure, even though the branch vessel prostheses 92a and 92b have not yet been set in place. When a physician is ready to introduce or deploy the branch vessel prostheses 92a and 92b to complete the procedure, or after the branch vessel prostheses 92a and 92b have been fully implanted, then the support 410 may be withdrawn from the patient.

The support 410 may be removed using a suitable technique such as pulling on a drawstring-like element to induce contraction of the support 410 to a smaller diameter and subsequent capture by a removal sheath. Alternatively, the distal end 414 of the support 410 may extend distally beyond the graft 20 such that the distal end 414 remains secured to the delivery device 70 throughout the procedure at a location distal to the graft 20, and then distal removal of the delivery device 70 (after placement of the branch vessel prostheses 92a and 92b) achieves a corresponding distal removal of the support 410.

In the embodiment of FIG. 9, as with the embodiment of FIGS. 7A-7B above, in the event that the branch vessel prostheses 92a and 92b cannot be placed into their respective coronary arteries 95a and 95b during an initial procedure, it is possible that the branch vessel prostheses 92a and 92b may be deployed at a later time in a subsequent procedure. In the interim, the support 410 may maintain a temporary channel to allow sufficient retrograde flow into the coronary arteries 95a and 95b to help sustain the patient's health.

As noted above, while one exemplary use of the prosthesis 10 has been shown with regard to the aortic annulus and ascending aorta for maintaining flow into the coronary arteries, the prosthesis 10 alternatively may be deployed in other parts of a patient's arterial or venous system, or any suitable duct, passageway or vessel, and the various systems 100, 200, 300 and 400 may maintain flow into branch vessels other than the coronary arteries depending on use of the prosthesis 10.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. An endoluminal prosthesis comprising:
    a graft having a tubular body comprising inflow and outflow ends, inner and outer surfaces, and partially and fully deployed states;
    a temporary channel disposed external to the outer surface of the graft in the partially deployed state, the temporary channel beginning at the outflow end of the graft, and extending along only a portion of a longitudinal length of the graft, and terminating before the inflow end of the graft,
    wherein the temporary channel is removed when the graft is in the fully deployed state, and
    at least one fenestration disposed in a sidewall of the graft between the inflow and outflow ends of the graft, wherein the temporary channel is aligned with the fenestration.

2. The prosthesis of claim 1, wherein the temporary channel comprises a "U"-shape.

3. The prosthesis of claim 1 further comprising a valve replacement disposed between the inflow and outflow ends of the graft.

4. The prosthesis of claim 1, wherein a shape of the temporary channel is maintained by securement of a first portion of the graft to a second portion of the graft.

5. The prosthesis of claim 4 wherein the first portion of the graft is secured to the second portion of the graft using at least one suture.

6. The prosthesis of claim 5 wherein the temporary channel is removed by breaking the suture using an external force.

7. The prosthesis of claim 1, wherein a shape of the temporary channel is maintained by securement of a portion of the graft to a delivery system.

8. The prosthesis of claim 7 further comprising a coupling member secured to the graft, and a wire extending along the delivery system, wherein the temporary channel is maintained when the wire is coupled to the coupling member of the graft, and wherein the temporary channel is removed when the wire is released from engagement with the graft.

9. The prosthesis of claim 1, wherein the temporary channel comprises a sheath having an aperture, wherein the aperture is disposed distal to the distal end of the graft in the partially deployed state, and a portion of the sheath is disposed adjacent to the outer surface of the graft in the partially deployed state.

10. An endoluminal deployment system comprising:
    a delivery device comprising a proximal end and a distal end;
    a graft having a tubular body comprising inflow and outflow ends, inner and outer surfaces, and partially and fully deployed states, and an inner lumen configured to facilitate fluid flow substantially in an antegrade direction;
    a temporary channel comprising inflow and outflow ends, the temporary channel disposed external to the outer surface of the graft in the partially deployed state, the temporary channel beginning at the outflow end of the graft, and extending along only a portion of a longitudinal length of the graft; and wherein the temporary channel is configured to receive fluid flow substantially in a retrograde direction,
    wherein the inflow end of the temporary channel is further away from the proximal end of the delivery device than the outflow end of the temporary channel,
    wherein the inner lumen of the graft is configured to facilitate fluid flow substantially in the antegrade direction through a main vessel, and wherein the temporary channel is configured to facilitate fluid flow substantially in the retrograde direction and into a branch vessel that branches off from the main vessel.

11. The deployment system of claim 10, wherein the temporary channel is removed when the graft is in the fully deployed state.

12. The deployment system of claim 10, further comprising at least one fenestration disposed in a sidewall of the graft between the inflow and outflow ends of the graft, wherein an inflow end of the temporary channel is aligned with the fenestration.

13. The deployment system of claim 10, wherein the temporary channel comprises a "U"-shape.

14. The deployment system of claim 10, wherein a shape of the temporary channel is maintained by securement of a first portion of the graft to a second portion of the graft.

15. The deployment system of claim 10, wherein a shape of the temporary channel is maintained by securement of a portion of the graft to a delivery system.

16. The deployment system of claim 10, further comprising a valve replacement disposed within at least a portion of the graft.

17. An endoluminal prosthesis comprising:
    a graft having a tubular body comprising proximal and distal ends, inner and outer surfaces, and partially and fully deployed states;
    a temporary channel disposed external to the outer surface of the graft in the partially deployed state, the temporary channel beginning at one of the proximal and distal ends of the graft, and extending along only a portion of a longitudinal length of the graft, wherein the temporary channel is removed when the graft is in the fully deployed state;
    wherein a shape of the temporary channel is maintained by securement of a first portion of the graft to a second portion of the graft;
    wherein the first portion of the graft is secured to the second portion of the graft using at least one suture; and
    wherein the suture comprises a biodegradable material, and the temporary channel is removed upon degradation of the suture.

18. An endoluminal prosthesis comprising:
    a graft having a tubular body comprising proximal and distal ends, inner and outer surfaces, and partially and fully deployed states;
    a temporary channel disposed external to the outer surface of the graft in the partially deployed state, the temporary channel beginning at one of the proximal and distal ends of the graft, and extending along only a portion of a longitudinal length of the graft, wherein the temporary channel is removed when the graft is in the fully deployed state;
    wherein the temporary channel comprises a removable stent framework disposed exterior to the graft in the partially deployed state.

* * * * *